United States Patent [19]

Eldridge

[11] Patent Number: 4,850,230

[45] Date of Patent: Jul. 25, 1989

[54] PULL TAB FORCE MEASURING APPARATUS

[75] Inventor: Lawrence B. Eldridge, Littleton, Colo.

[73] Assignee: Adolph Coors Company, Golden, Colo.

[21] Appl. No.: 245,904

[22] Filed: Sep. 19, 1988

[51] Int. Cl.$^4$ .............................................. G01N 3/08
[52] U.S. Cl. ..................................................... 73/835
[58] Field of Search ................. 73/826, 834, 835, 827, 73/837

[56] References Cited

U.S. PATENT DOCUMENTS 3,464,261  9/1969  Helms .................................... 73/835
4,637,260  1/1987  Gilliam et al. ......................... 73/826

OTHER PUBLICATIONS

Product Inspection Gauges, May 1974, Can Division Reynolds Metals Company.

*Primary Examiner*—Jerry W. Myracle
*Attorney, Agent, or Firm*—Klaas & Law

[57] ABSTRACT

Apparatus for measuring the forces applied to a pull tab during the formation of an opening in a container lid having an upper and lower surface with a pull tab hingedly secured on the upper surface and a score line in the container lid defining an opening and wherein one container lid at a time is fed into a holder having an opening therein so that a substantial portion of the upper surface of the container lid and all of the pull tab are exposed. A rotatable pull tab positioning head having a generally planar surface in which a recess in the shape of pull tab is formed is moved into resilient contact with the pull tab and is rotated relative to the container lid until the pull tab moves into the recess and thereafter the container lid and pull tab rotate with the positioning head to position the pull tab at a predetermined location. A load cell assembly having a pivotal hook member is moved into position with the hook member between the upper surface of the container lid and the pull tab. The container lid is rotated about the axis of the hinge connection of the pull tab and the hook member is held at a fixed position. As the container lid rotates, the hook member applies resistant forces on the pull tab until the opening is formed in the container lid which resistant forces are measured by the load cell assembly. The opened container lid is then discharged from the holder.

20 Claims, 8 Drawing Sheets

PULL TAB FORCE MEASURING APPARATUS

FIELD OF THE INVENTION

This application is directed generally to the field of force measuring apparatus and more particularly to force measuring apparatus for measuring the force applied to a pull tab to form an opening in a container lid.

BACKGROUND OF THE INVENTION

There are many containers or cans manufactured daily that are filled and then sealed with a can end or lid. These container lids are provided with pull tabs for forming an opening in the container lid which opening in the container lid is defined by a score line. The pull tabs may be of the stay-on-tab style, the throw away tab style, the complete panel removal style and other styles. In all instances, it is desired that there is some resistance to moving the pull tab to form the opening in the container lid but not so much resistance that the opening is too hard to form or cannot be formed or too little resistance that the container lid will prematurely open. In order to ensure customer satisfaction in the forming of openings in the container lids, it is customary to test daily many thousands of container lids to ensure that the manufacturing apparatus for making the container lids is functioning properly. One testing apparatus is marketed by Continental Can Co. and comprises a hand operated device which is subject to human operational variances. There exists a need for apparatus which would function to operate on each container lid to be tested in the same manner so that consistent test results could be obtained.

BRIEF DESCRIPTION OF THE INVENTION

This invention provides apparatus for measuring the force applied to a pull tab to form an opening in a container lid wherein a container lid is automatically positioned in a holding means so that the pull tab is properly oriented and a hook member of a force measuring apparatus is automatically positioned between the upper surface of the container lid and the pull tab and the hook member is then functionally retained in a fixed position. The container lid is rotated at a constant speed to move away from the pull tab and the hook member applies a restraining force on the pull tab while the opening is being formed in the container lid. The force measuring apparatus continuously measures the restraining force being applied by the hook member at each angular relationship between the pull tab and the container lid during the opening cycle and records such measurements on an electronic reproducing device and makes a printed record thereof.

In a preferred embodiment of the invention, the apparatus for measuring the force applied to a pull tab to form an opening in a container lid comprises a feed chute for holding a supply of container lids, each of which has an upper surface, a lower surface, and a peripheral rim portion and a pull tab on the upper surface which pull tab is adapted to be grasped so as to apply a force thereto to form an opening in the container lid. Holding means are provided for holding one of the container lids while operations are performed thereon. The holding means has at least one opening formed therein so that a substantial portion of the upper surface and all of the pull tab are exposed. Feed means are provided for separating one of the container lids from the supply thereof and feeding the one container lid to the holding means. Stop means are provided to position the one container lid in the holding means so that the substantial portion of the upper surface and the pull tab are exposed through the at least one opening.

Orienting means are provided for contacting the upper surface and the pull tab to position the pull tab at a predetermined location in the holding means. The orienting means has a body portion which is mounted for reciprocal movement in linear directions. A pull tab positioning head is resiliently mounted on the body portion for movement therewith into and out of contact with the upper surface of the container lid and the pull tab. Rotating means are provided for rotating the pull tab positioning head about a longitudinal axis. The pull tab positioning head has a generally planar surface facing the opening in the holding means and a recess having a shape corresponding to that of the pull tab is formed i the generally planar surface. Control means are provided for positioning the pull tab positioning head so that at the end of each operation of the pull tab positioning head the detent will always be located at the predetermined location. After the pull tab positioning head has been moved into resilient engagement with the pull tab on the upper surface of the container lid in the holding means, the pull tab positioning head is rotated through one complete revolution of three hundred and sixty degrees. At the beginning of the revolution, the pull tab positioning head will rotate relative to the pull tab and the container lid in the holding means until the pull tab enters the recess after which the pull tab and the container lid rotate with the pull tab positioning head so that at the end of the one complete revolution the recess and therefore the pull tab are at the predetermined location. If desired, the pull tab positioning head and the pull tab and container lid are rotated through another complete revolution of three hundred and sixty degrees during which printing means print an identification on the lower surface of the container lid. After the printing operation, the pull tab positioning head is moved out of the way and pull tab holding means are moved into position to continue the opening operations.

Slidably mounted force measuring means are then moved into position. The force measuring apparatus has a pivotally mounted hook member that is positioned between the pull tab and the container lid. After being positioned, the hook member is functionally restrained from movement during the force measuring operation. Although the hook member is restrained from movement, it is mounted on a ball slide assembly that is theoretically free to move in one direction. The holding means are then rotated to cause relative movement between the container lid and the pull tab to apply the force required to form the opening in the container lid. The hook member is operatively connected to measuring apparatus which measures the restraining force on the hook member as it holds the pull tab in a fixed position while the container lid is being rotated. Recording means, such as an electronic reproducing device and a printer, are provided to record the restraining forces applied to the pull tab during the formation of the opening in the container lid. Discharge means are provided for discharging the opened container lid into a hopper.

BRIEF DESCRIPTION OF THE DRAWINGS

An illustrative and presently preferred embodiment of the invention is shown in the accompanying drawings in which.

DETAILED DESCRIPTION OF THE INVENTION

Figure 1:
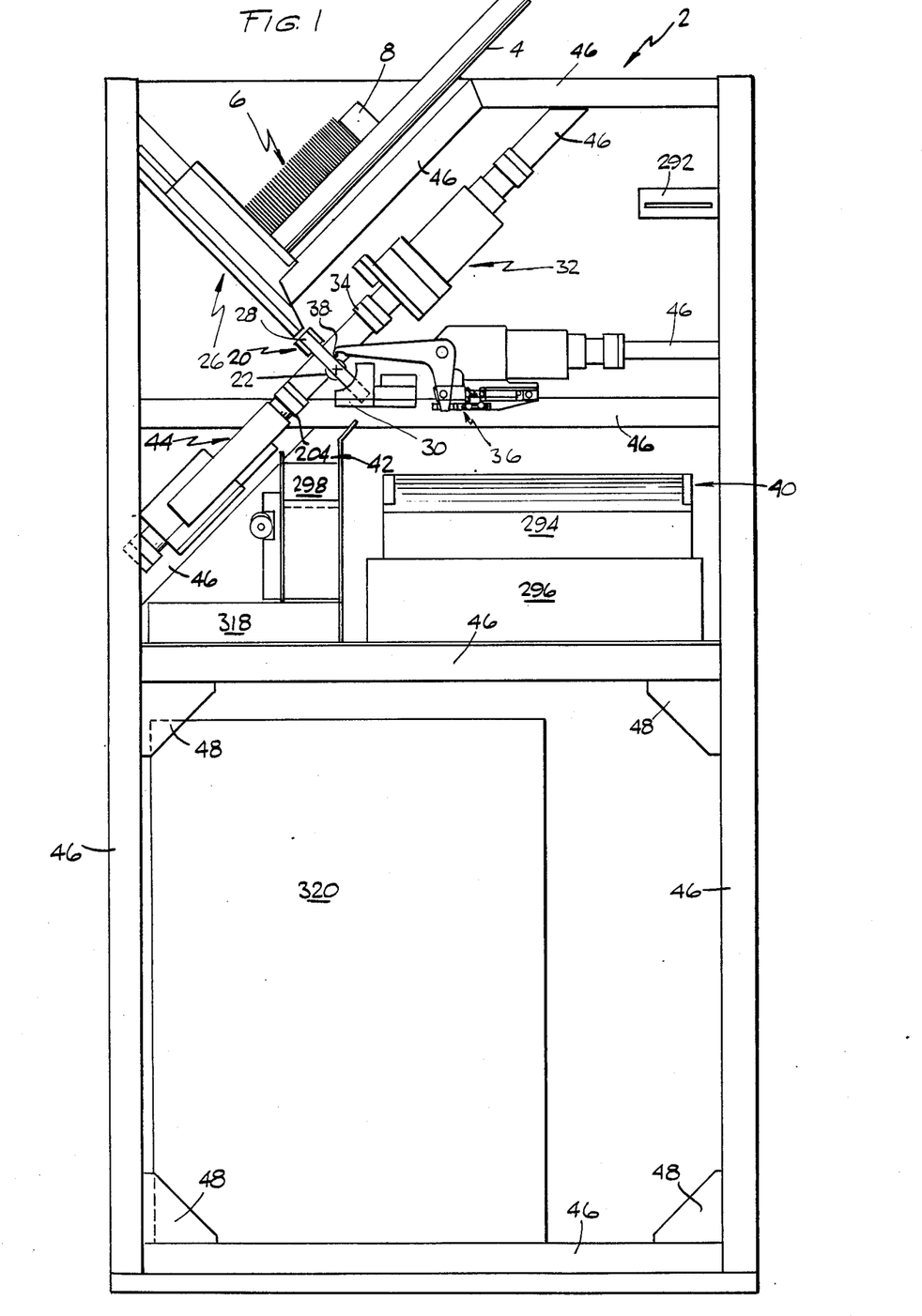
FIG. 1 is a front elevational view of the preferred embodiment of the invention.
Figures 2, 3, 4:
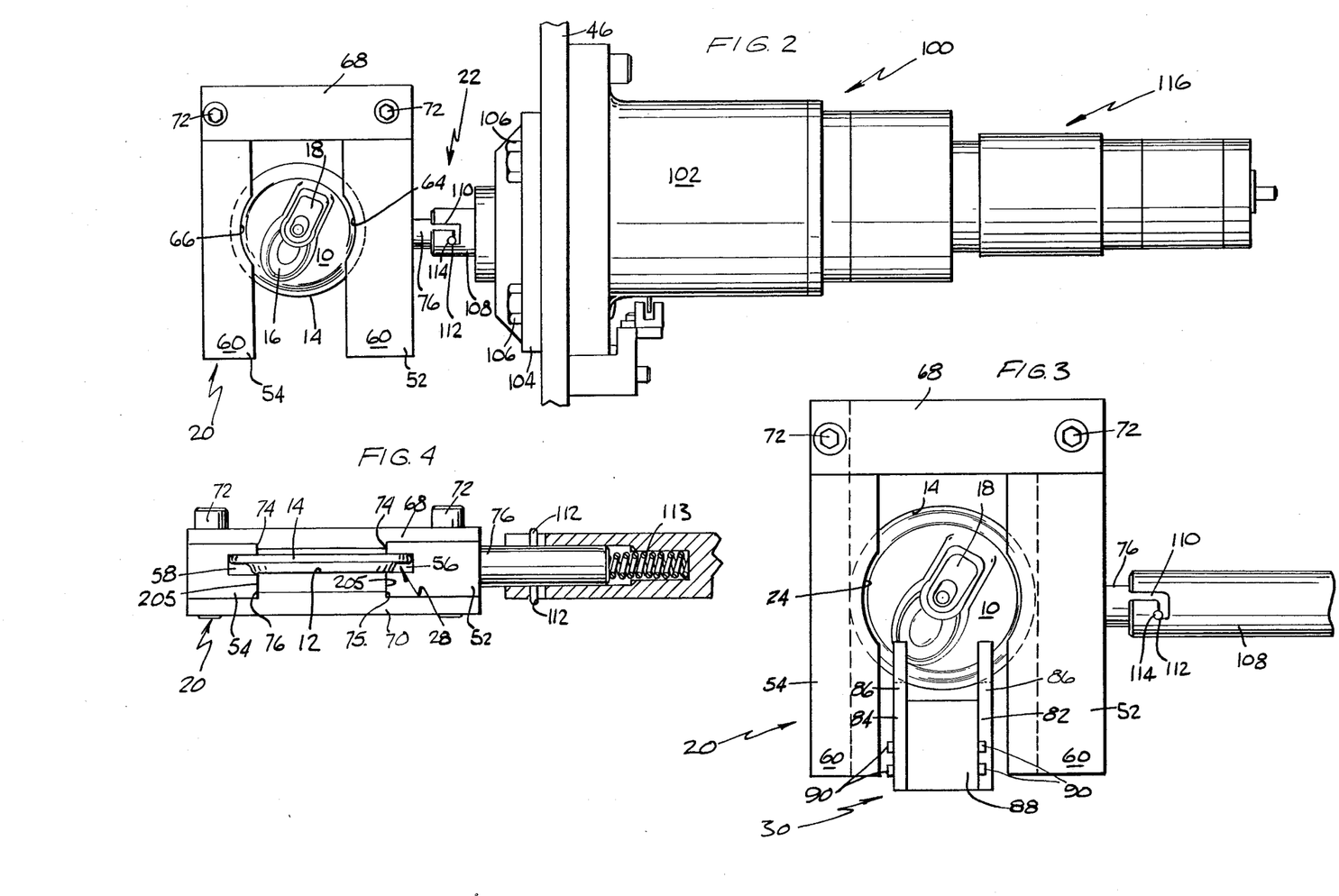
FIG. 2 is a side elevational view of the holding means and the rotating means therefor.
FIG. 3 is an enlarged view of a portion of FIG. 2.
FIG. 4 is a top plan view of FIG. 3 with parts in section.

The preferred embodiment of the invention is illustrated by a front elevational view in FIG. 1 and comprises apparatus 2 for measuring the force applied to a pull tab to form an opening in the container lid. A feed chute 4 holds a supply of container lids 6 for gravity feed assisted by a separate weight 8. As illustrated in FIGS. 3 and 4, each of the container lids has an upper surface 10, a lower surface 12, a peripheral rim portion 14, a severable tab portion 16 and a pull tab 18 secured to the container lid 6 and extending over a part of the upper surface 10, which pull tab 18 is adapted to be grasped so as to apply a force thereto acting against the severable tab portion 16 to form an opening in the container lid 10.

Holding means 20 are provided for holding a container lid 6 at different locations while various operations are performed thereon. The holding means 20 are mounted for rotation about a fixed axis on rotation means 22 described more fully below. As illustrated in FIGS. 2-4, the holding means 20 have at least one opening 24 formed therein so that a substantial portion of the upper surface 10 and all of the pull tab 18 are exposed. Feed means 26, of a conventional type, are provided for separating one of the container lids 6 from the supply and feeding such container lid 6 to a passageway 28 in the holding means 20. Stop means 30 are provided and function to limit the movement of the container lid 6 through the passageway 28 so that the substantial portion of the upper surface 10 and all of the pull tab 18 are exposed through the opening 24.

Orienting means 32 are provided and have a pull tab positioning head 34 which is rotatably mounted on the orienting means 32 and is dimensioned so that it may pass through the opening 24 and move into contacting relationship with the upper surface 10 and the pull tab 18. As explained more fully below, the pull tab positioning head 34 is rotated when in contact with the upper surface 10 and the pull tab 18 to position the pull tab 18 of each of the container lids 6 at the same predetermined position.

Force measuring means 36 are provided for measuring the forces generated during the formation of the opening in the container lid 6. The force measuring means 36 has a pivotally mounted hook member 38 which, as explained more fully below, is positioned between the upper surface 10 and the pull tab 18 and restrains the movement of the pull tab 18 during the force measuring operation. After the hook member 38 has been moved into position between the upper surface 10 and the pull tab 18, the holding means 20 are rotated to move the upper surface 10 in a direction away from the pull tab 18 so as to generate the forces to be applied to the severable tab portion 16 to form the opening in the container lid 10. The force measuring means 36 measures the restraining force on the hook member 34 as it prevents movement of the pull tab 18. The force measuring means 36 are operatively associated with recording means 40 for continuously recording the forces applied during the opening operation. Discharge means 42 are provided and, as explained below, have means for separating the container lids 6 into passed or failed categories.

In operation, the holding means 20 is positioned at an angle of about 45 degrees to the horizontal. The feed means 26 feeds one container lid 6 into the passageway 28 and the one container lid 6 moves through the passageway 28 until it contacts the stop means 30. The orienting means 32 is then moved toward the holding means 20 so that the pull tab positioning head 34 moves into contacting relationship with the upper surface 10 and the pull tab 18. As explained more fully below, the pull tab positioning head 34 makes one complete revolution of 360 degrees to position the pull tab at a predetermined location. If desired, inking means 44 are provided and the pull tab positioning head 34 will make a second complete revolution of 360 degrees during which information will be printed on the bottom surface 12 of the container lid 6. At the completion of the second revolution, the pull tab 18 will be at the same predetermined location. The orienting means 34 is then moved to an out of the way location as illustrated in FIG. 1. The holding means 10 is then rotated so that it is positioned at an angle of about 90 degrees to the horizontal. The force measuring means 36 are then moved into the measuring position with the hook member 38 in a raised upper position and is then pivoted downwardly into a lower position between the upper surface 10 and the pull tab 18 to restrain movement of the pull tab 18 during the force measuring operation. The holding means 20 are then rotated to move the upper surface 10 in a direction away from the pull tab 18 so as to generate the forces to be applied to the severable tab position 16 to form the opening in the container lid 10. The force measuring apparatus 34 measures the restraining force on the hook member 34 as it prevents movement of the pull tab 18. The holding means 20 are rotated through ninety degrees until the holding means 20 are substantially even with the horizontal. Recording means 40 continuously records all restraining forces during the rotation of the holding means 20 through the ninety degrees. The holding means 20 is then rotated back to the 90 degree position to the horizontal and the hook member 38 is raised to its upper position and the force measuring means 36 are moved to an out of a way position. The holding means 20 are then rotated a sufficient amount so that the container lid 6 no longer contacts the stop means 30 and may fall out of the holding means 20 into the discharge means 42 where they are separated into passed or failed categories.

As illustrated in FIG. 1, there are provided support structures for supporting the various components of the invention and comprise a plurality of support beams 46 which are held in a desired assembled relationship by suitable means such as by welding (not shown) and reinforced where necessary by gusset plates 48.

The holding means 20 are illustrated in FIGS. 2-5 and comprises a pair of spaced apart arm portions 52 and 54 having facing longitudinally extending slots 56 and 58 to form the passageway 28. Each of the arm portions 52 and 54 has an upper surface 60 and a lower surface 62. The arm portion 52 has an arcuate cut-out portion 64 and the arm portion 54 has an arcuate cut-out portion 66 to form the one opening 24. An upper member 68 and a lower member 70 extend between the arm portions 52 and 54 and are secured thereto by headed threaded bolts 72 secured in threaded openings (not shown) in the lower member 70. The upper member 68 has spaced apart recesses 74 and the lower member 70 has spaced apart recesses 75 so that portions of the arm portions 52 and 54 can abut against the recesses 74 and 75 and be held in the proper spaced apart relationship. A rod 76 projects outwardly from the arm portion 52 and is integral with or secured thereto which rod 76 has a longitudinal axis which provides the axis of rotation of the holding means 20 as described below.

Figures 5, 6:
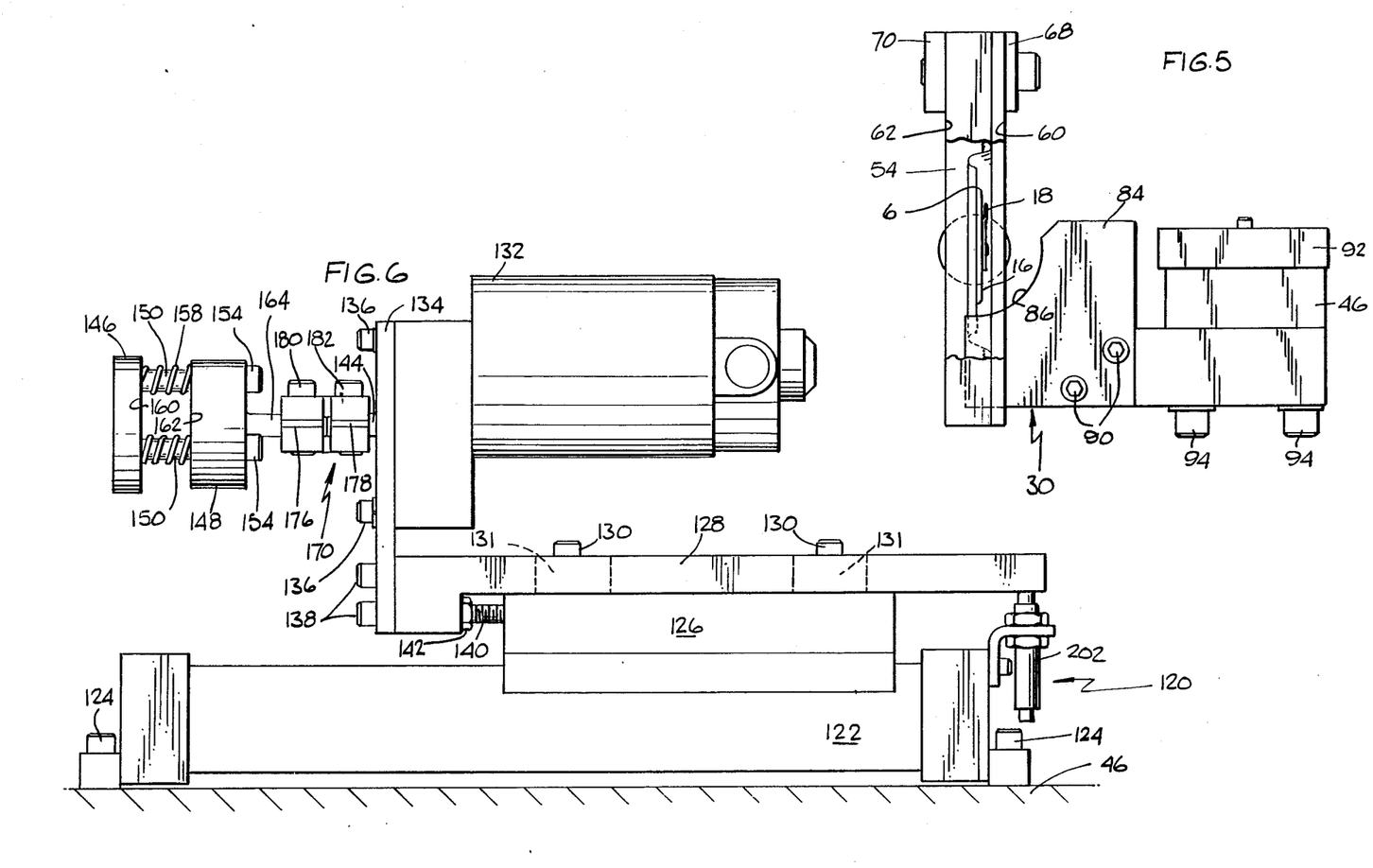
FIG. 5 is a front elevational view illustrating the holding means and the stop means.
FIG. 6 is a side elevational view of the pull tab orienting means.
Figure 7:
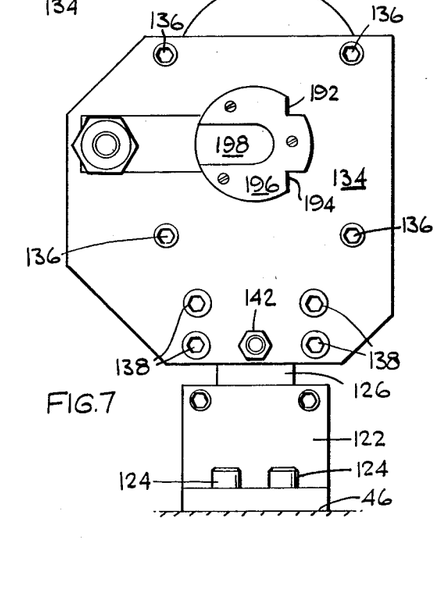
FIG. 7 is a front elevational view of FIG. 6.

The stop means 30, illustrated in FIGS. 3 and 5, comprise a pair of spaced apart plate members 82 and 84 having arcuate surfaces 86 adapted to be contacted by the peripheral rim portion 14 of each container lid 6. The plate members 82 and 84 are secured to a support block 88 by headed threaded bolts 90 secured in threaded openings (not shown) in the support block 88. The support block 88 is mounted on a portion of a support beam 46 by suitable means such as a clamping plate 92 and threaded bolts 94.

In FIG. 2, there is illustrated a drive means 100 for rotating the holding means 20 to various positions to have suitable operations performed on a container lid 6. The drive means 100 comprises a motor 102 fixedly mounted on a support beam 46 by a plate member 104 and headed threaded bolts 106. A rotatable shaft 108 extends outwardly from the motor 102 and has a spring urged bayonet type joint 110 for receiving pins 112 which project radially outwardly from the rod 76. In assembly, the rod 76 with the pins 112 is pushed inwardly against the spring 113 of the bayonet type joint 108 and rotated until the pins 112 are secured in notches 114 in the bayonet type joint 108. Computer control means 116 are provided for controlling the rotation of the holding means 20.

The orienting means 32 are illustrated in FIGS. 6-9 and comprise a conventional computer operated slide assembly 120 such as a Lintra Rodless Cylinder C/45025-EL-EL-4.0 comprising a base 122 mounted on a support beam 46 which extends at an angle of 45 degrees to the support beam 46 of the stop means 30 and is secured to the support beam 46 by threaded bolts 124. A slide member 126 is mounted for reciprocal linear sliding movement over the base 122. A mounting bracket 128 is secured to the slide member 126 for movement therewith by headed threaded bolts 130 which pass through slots 131 to allow for adjustment of the mounting bracket 128 on the slide 126. A motor 132 is mounted on a support bracket 134 by headed threaded bolts 136 which support bracket 134 is secured to the mounting bracket 128 by threaded bolts 138. An adjusting bolt 140 having a hexagonal head 142 is provided for adjusting the position of the mounting bracket 128 on the slide member 126. A rotatable shaft 144 projects outwardly from and is rotated by the motor 132. A pull tab positioning head 146 is resiliently mounted on a base support member 148. A plurality of rods 150 are slidably mounted in bores 152 and have enlarged head portions 154 on one end thereof for preventing the sliding movement thereof into the base support member 148. The other end of the rods 150 are threadedly secured in threaded openings 156 in the pull tab positioning head 146. A coiled spring 158 is positioned around each of the rods 150 and bears against the surface 160, FIG. 6, of the pull tab positioning head 146 and the surface 162 of the base support member 148 to urge the surface 160 away from the surface 162 to provide for the resilient mounting of the pull tab positioning head 146. A shaft 164 extends outwardly from the base support member 148.

Figure 9:
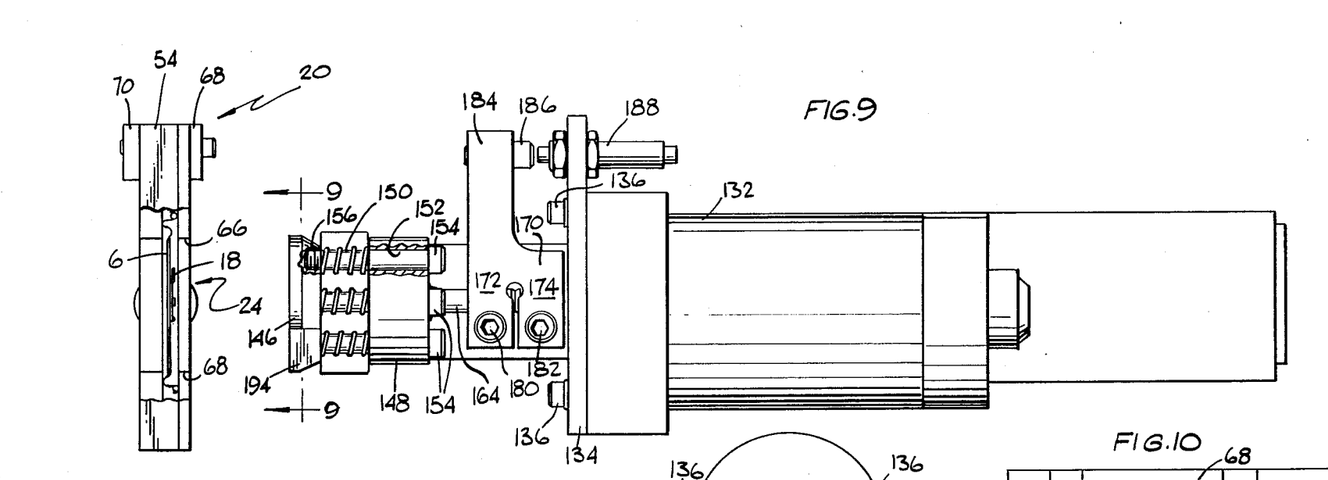
FIG. 9 is a top elevational view illustrating the relative locations of the pull tab orienting means and the holding means.

A coupling 170 is used to connect the shaft 164 onto the shaft 144 for rotation therewith. As illustrated in FIGS. 6 and 9, the coupling 170 has bifurcated arm portions 172 and 174, each of which has end separations 176 and 178 so that the shafts 164 and 144 may be slidably moved into the arm portions 172 and 74 and then clamped in position thereon by threaded bolts 180 and 182. This permits accurate positioning of the pull tab positioning head 146. Extending outwardly from the coupling 170 is a bracket arm 184 in which is mounted an outwardly projecting cylindrical member 186. A proximity sensor 188 is mounted on the support bracket 134 and is aligned with the cylindrical member 186 for positioning the pull tab positioning head 146. The motor 132 is programmed to rotate the shaft 144 and therefore the shaft 164 through one complete revolution of 360 degrees starting from the location of the proximity sensor 188.

Figure 8:
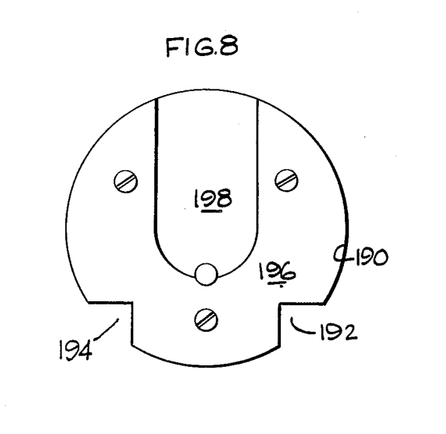
FIG. 8 is a front elevational view of a pull tab positioning head.

One type of a pull tab positioning head 146 is illustrated in FIG. 8 and has a generally circular peripheral surface 190 except for two cut-out portions 192 and 194 to permit passage thereof through the stop means 30. The pull tab positioning head 146 has a generally planar surface 196 having a recess 198 formed therein which recess 198 has a configuration slightly larger than a pull tab 18 so that a pull tab 18 can readily enter into the recess.

Figure 10:
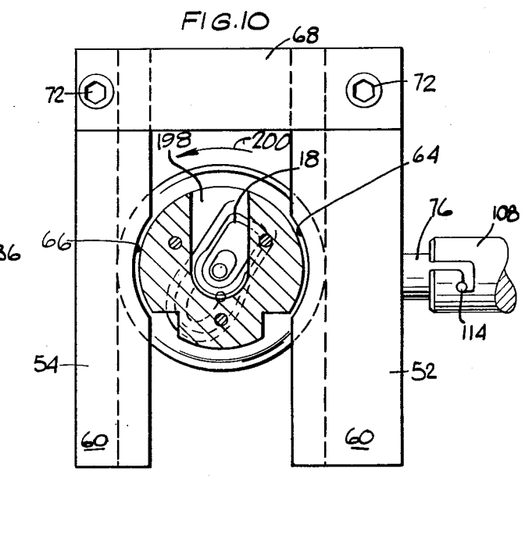
FIG. 10 is a cross-sectional view taken on the line 9—9 of FIG. 8.

As illustrated in FIG. 9, the holding means 20 are in position so that the positioning head can be moved through the opening 24 into contact with the upper surface 10 of the container lid 6 and the pull tab 18. In FIG. 10, there is illustrated the relative positions of the pull tab 18 in the holding means 20 and the recess 198 in the pull tab positioning head 146 prior to the rotation of the positioning head 146. After the pull tab positioning head 146 has moved into contact with the upper surface 10 of the container lid 6 and the pull tab 18, the motor 132 will rotate the pull tab positioning head 146 one complete revolution of 360 degrees in a counter-clockwise direction as indicated by the arrow 200. During the first part of the rotation, the pull tab positioning head will rotate relative to the container lid 6 until the pull tab 18 is opposite to the recess 198. This relative rotation is accomplished by the resilient mounting of the pull tab positioning head 146 and the materials in the pull tab positioning head 146, the container lid 6 and the arm portions 52 and 54. When the pull tab positioning head 146 contacts the pull tab 18, it pushes the lower surface 12 of the container lid 6 against the surfaces defining the slots 56 and 58. The frictional forces between the lower surface 12 and the surfaces defining the slots 56 and 58 are greater than the frictional forces between the planar surface 19 of the pull tab positioning head 146 and the pull tab 18. This is largely so since the initial contact between the pull tab positioning head 146 and the planar surface 196 is primarily against the pull tab 18. During the rotation of the pull tab positioning head 146, the pull tab 18 will enter into the recess 198. Thereafter, the container lid 6 will rotate with the pull tab positioning head 146. Since the recess 198 is always returned to the same location, the pull tab 18 will always be moved to the same predetermined location in the holding means 20. After the pull tab 18 has been positioned, the pull tab positioning head 146 is moved to an out of the way location by the slide member 126. A limiting sensor 202 mounted on the base 122 controls the movement of the slide member 126.

In some operations, it is desired to print identification on the lower surface 12 of the container lid 6. This is accomplished by the apparatus illustrated in FIG. 1. A conventional printing apparatus 44 is mounted on a support beam 46 for reciprocal movement in linear directions. In the normal position, the printing head 204 is located away from the holding means 20. When it is desired to perform the printing operation, the holding means 20 is at an angular relationship of 45 degrees to the horizontal and the printing head 204 is moved into close proximity with the lower surface 12 of the container lid 6. The arm portions 52 and 54 have arcuate cut-out portions 205 similar to the arcuate cut-out portions 64 and 66 to provide a second opening similar to the one opening 24. After the printing head 204 has been moved into position, the pull tab positioning head 146 is rotated through one complete revolution of 360 degrees. The container lid 6 rotates with the pull tab positioning head 146 and the desired information is printed on the lower surface 12. After the printing operation has been performed, the printing apparatus 44 is moved to an out of the way location.

Figure 11:
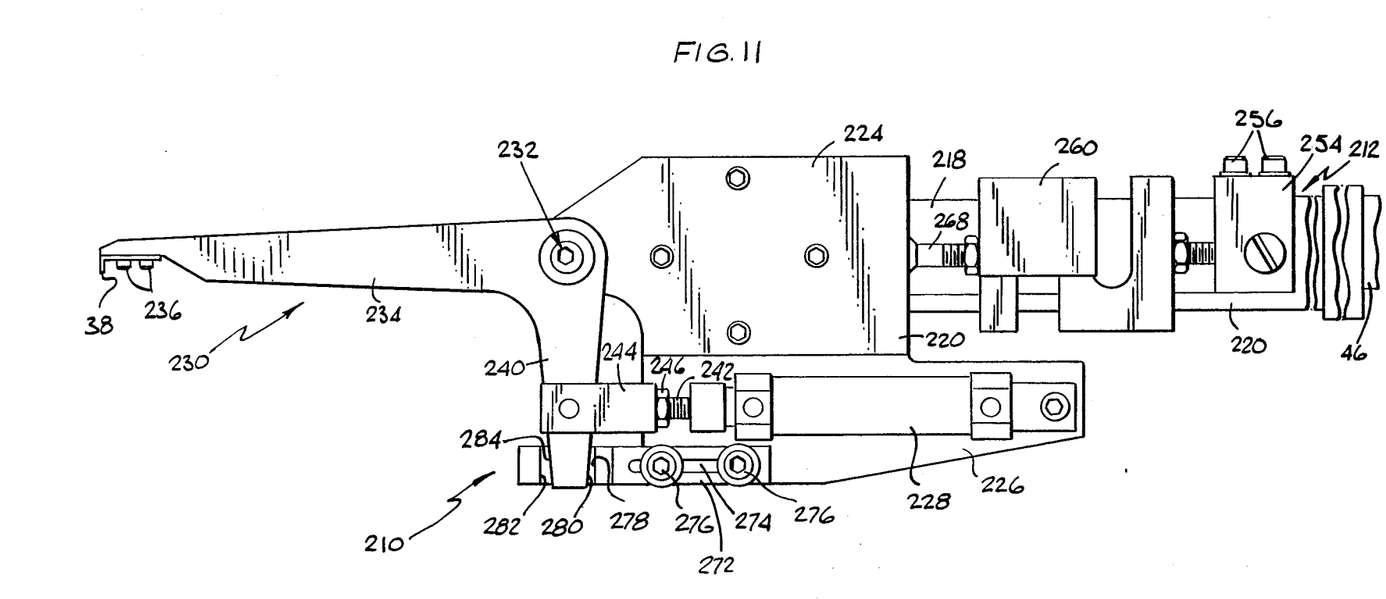
FIG. 11 is a side elevational view of the force measuring apparatus.
Figure 12:
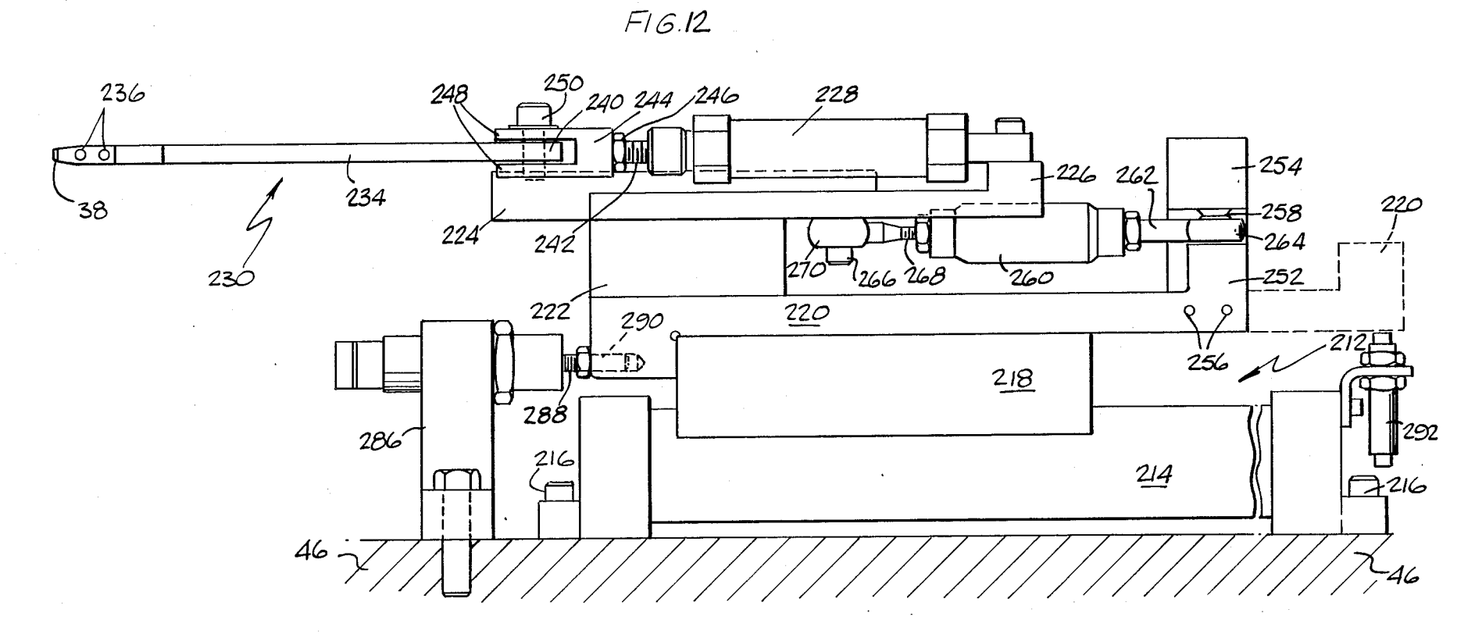
FIG. 12 is a bottom plan view of FIG. 9.

The force measuring means 210 are illustrated in FIGS. 11 and 12 and comprise a conventional computer operated slide assembly 212 such as a Lintra Rodless Cylinder C/45025-EL-EL-4.0 comprising a base 214 mounted on a support beam 46 by headed threaded bolts 216. A slide member 218 is mounted for reciprocal linear sliding movement over the base 214. A mounting bracket 220 is secured to the slide member 218 for movement therewith. A conventional ball slide assembly 222, such as a Daedal Ball Slide 4501, has one portion thereof mounted on the mounting bracket 220 and the other portion thereof mounted on a support plate 224 so that the support plate 224 is theoretically free to move relative to the mounting bracket 220 in response to forces applied thereto. The support plate 224 has an extension support member 226 on which is mounted an air cylinder 228. An L-shaped lever 230 is pivotally mounted on the support plate 224 by pivot means 232 such as a pivot pin or a bearing. The L-shaped lever 230 has a first arm portion 234 on which is mounted the hook member 38 by headed threaded bolts 236 received in threaded openings (not shown) in the first arm portion 234. The L-shaped lever 230 has a second arm portion 240. The air cylinder 228 has a threaded actuating rod 242 which is moved by the air cylinder 228 in linear directions. A connecting member 244 is adjustably mounted on the threaded actuating rod 242 by the nut 246 for movement with the actuating rod 242. The connecting member 244 has a bifurcated portion 248 in which is mounted a pivot pin 250. The L-shaped lever 230 is rotatably mounted on the pivot pin 250.

The mounting bracket 220 has an outwardly projecting extension member 252 to which is fixedly secured a plunger bracket 254 by headed threaded bolts 256. A pivot pin 258 projects outwardly from the plunger bracket 254. A load cell 260, such as an Interface Load Cell SM-10, has a threaded first connecting rod 262 extending outwardly therefrom and has a rotatable means 264, such as a bearing, which is rotatably mounted on the pin 258. Another pin 266 extends outwardly from and is fixedly secured on the support plate 224. The load cell 260 has a threaded second connecting rod 268 extending outwardly therefrom and has a rotatable means 270, such as a bearing, which is rotatably mounted on the pin 266. The load cell 260 measures the force applied to the hook member 38 as described below. An adjustable stop member 272, FIG. 11, is mounted on the extension support member 226 and has an elongated slot 274 therein. A pair of spaced apart headed threaded bolts 276 pass through the slot 274 and are received in threaded openings (not shown) in the extension support member 226. The stop member 272 has a surface portion 278 adapted to be contacted by the surface portion 280 on the second arm portion 240. The stop member 272 also has a surface portion 282 adapted to be contacted by the surface portion 284 on the second arm portion 240.

Figure 13:
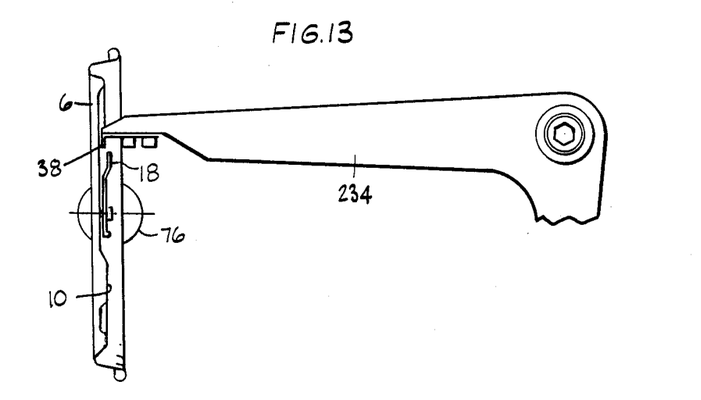
FIGS. 13-15 illustrate the relative locations of the hook member, the pull tab and the container lid during the force measuring operation.
Figure 14:
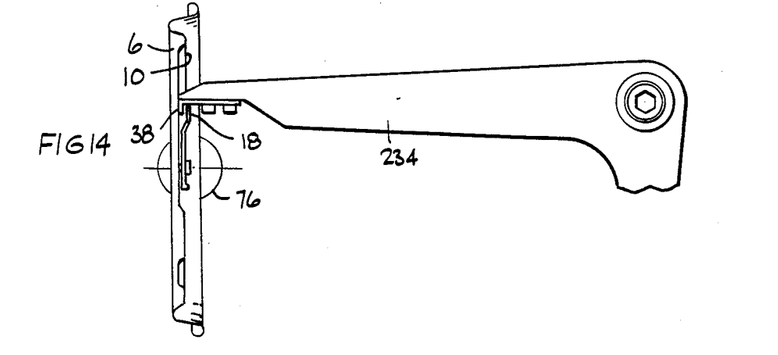
Figure 15:
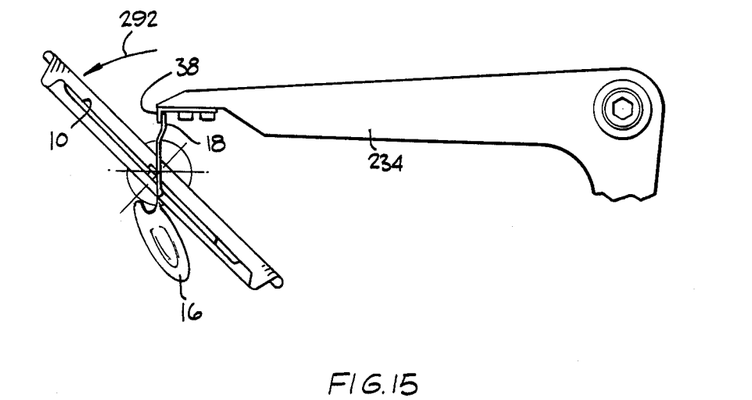

In operation, the slide member 218 is normally located to the right side as illustrated in dotted outline in FIG. 12 so that the force measuring apparatus 210 is in an out of the way location. When it is desired to form the opening in the container lid 6, the slide member 218 is moved to the left as illustrated in FIG. 12. A shock absorber 286 is fixedly mounted on a support beam 46 and has an adjustable stopping rod 288 projecting outwardly therefrom and located so as to enter a recess 290 in the mounting bracket 220 so as to stop the movement of the slide member 218. A proximity sensor 292 is used to sense the presence of the mounting plate 220. The operation of the L-shaped lever 230 is illustrated in FIGS. 13-15. The pivotal movement of the L-shaped lever 230 is controlled by the air cylinder 228. In its normal position, the surfaces 282 and 284, FIG. 11, of the L-shaped lever 30 are in contacting relationship so that the first arm portion 234 is in the raised location as illustrated in FIG. 13. After being positioned next adjacent to the container lid 6, the L-shaped lever 230 is pivoted by the air cylinder 228 and the surface 280 is moved toward the surface 278 so that the first arm portion 234 is in its lowered location with the hook member 38 located between the pull tab 18 and the upper surface 10 of the container lid 6 as illustrated in FIG. 14. If no container lid 6 or pull tab 18 is present, the movement of the surface 280 is stopped by contact with the surface 278. After the hook member 38 has been positioned as illustrated in FIG. 14, the holding means 20 and therefore the container lid 6 are rotated through 90 degrees in the direction indicated by the arrow 292 to form the opening in the container lid 6. In FIG. 15, the container lid 6 has been rotated through about 45 degrees and the severable tab position 16 has been partially moved to its final position after forming the opening in the container lid 6.

As illustrated in FIGS. 14 and 15, the hook member 38 remains in a fixed position during the rotation of the container lid 6. As described above, the support plate 224 is theoretically free to move in a direction toward the container lid 6, but such movement is prevented by the load cell 260. While restraining movement of the support plate 224, the load cell 260 measures the forces being applied to the hook member 38 by the rotation of the container lid 6. The load cell sends out continuous signals of the forces being applied throughout the 90 degree rotation of the container lid 6. These signals are sent to an electronic reproducing device 292, such as a floppy disk, and a recorder-printer 294 which continuously prints the information on the paper from the paper box holder 296.

Figure 16:
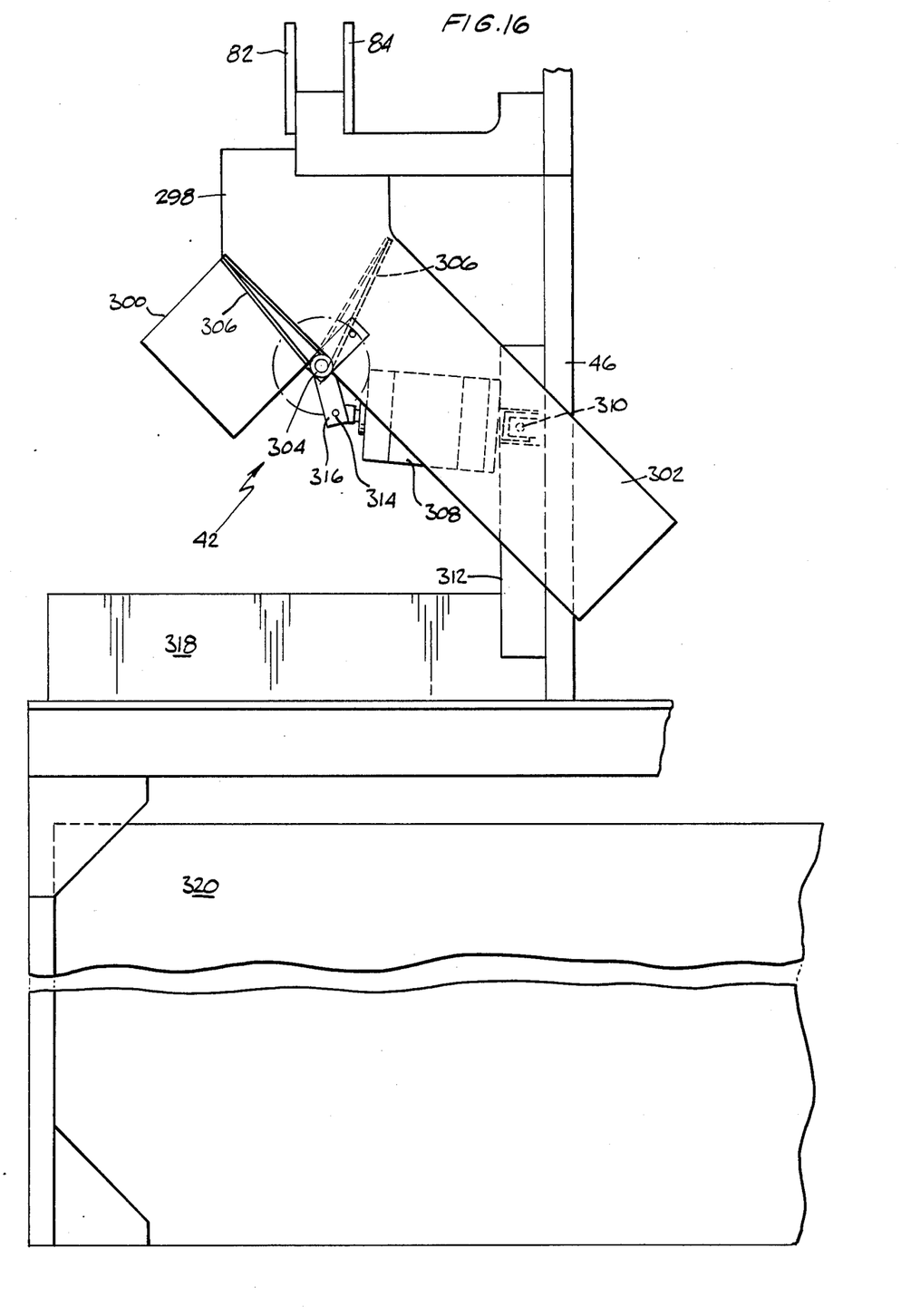
FIG. 16 is a side elevational view of the discharge means.

The discharge means 42 is illustrated in FIGS. 1 and 16. After the holding means 20 have been rotated through the 90 degrees of rotation to form the opening in the container lid 6, the air cylinder 228 moves the L-shaped lever 230 so that the surfaces 282 and 284 are in contacting relationship so that the first arm portion 234 is in the raised location and the hook member 38 is away from the pull tab 18. The force measuring means 210 are then moved by the slide member 218 to the out of the way location. The holding means 20 are then rotated in a clockwise direction, looking at the illustration in FIG. 1, through an arc of about 100 degrees so that the peripheral rim portion 14 of the container lid 6 is no longer in contact with the plate members 82 and 84 of the stop means 30 so that the container lid 6 is free to fall through the passageway 28 out of the holding means 20 into a discharge chute 298. The discharge chute 298 has two branches 300 and 302 with failed container lids 6 passing through branch 300 and passed container lids 6 passing through branch 302. A rotatable shaft 304 is mounted at the juncture of branches 300 and 302 and a chute diverter 306 is mounted on the rotatable shaft 304 for rotation therewith. An air cylinder 308 is pivotally mounted by pivot means 310 on a bracket 312 which is fixedly attached to a support beam 46. The air cylinder 308 is also pivotally mounted by pivot means 314 on a lever arm 316 which is secured to the rotatable shaft 304 so that movement of the lever arm 316 rotates the rotatable shaft 304. The air cylinder 308 is programmed to rotate the chute diverter 306 to open or close the branches 300 and 302. The chute diverter 306 is normally in a position to close branch 300. A relatively small hopper 318 is located to receive container lids 6 passing through the branch 300 and a relatively large hopper 320 is located to receive container lids 6 from the branch 302. The air cylinder 308 responds to a signal received from the force measuring apparatus 210 to move the chute diverter 306 from its normal position closing branch 300 to a position opening branch 300 and closing branch 302. After a time interval sufficient to allow a failed container lid 6 to pass through the branch 300, the air cylinder 308 moves the chute diverter 306 back to its normal position closing branch 300.

The operational sequence of the various components may be controlled by a standard computer system which forms no part of this invention. Such a system could be an STO Bus industrial microcomputer system using a CPU card containing an 8088 cpu chip which runs a DOS operating system. The majority of the software would be located in an EPROM permanent ram memory. The control system could utilize a 360 kbyte 5¼ floppy disk for user input and for data output.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. Apparatus for measuring the force applied to a pull tab to form an opening in a container lid comprising:
   a feed chute for holding a supply of container lids, each of which has an upper surface, a lower surface, a peripheral rim portion, a severable tab portion and a pull tab secured to said container lid and extending over a part of said upper surface which pull tab is adapted to be grasped so as to apply a force thereto acting against said severable tab portion to form an opening in said container lid;
   holding means for holding one of said container lids while operations are performed thereon;
   said holding means having at least one opening formed therein so that a substantial portion of said upper surface and all of said pull tab are exposed;
   feed means for separating one of said container lids from said supply thereof and feeding said one of said container lids to said holding means;
   stop means for cooperating with said holding means for positioning said one container lid so that said substantial portion of said upper surface and said pull tab are exposed through said at least one opening;
   orienting means for contacting said pull tab and said upper surface to position said pull tab at a predetermined location in said holding means;
   force measuring means having a portion thereof in contact with said pull tab for measuring the forces generated on said pull tab during the formation of said opening in said container lid;
   force applying means for causing relative movement between said container lid and said pull tab to apply a force to said severable tab portion to form said opening in said container lid;
   recording means for recording the forces applied to the pull tab during the formation of the opening in said container lid; and
   discharge means for discharging said opened container lid to a hopper.

2. Apparatus as in claim 1 wherein said holding means comprises:
   a pair of spaced apart arm portions;
   an upper member and a lower member secured to said pair of spaced apart arm portions to hold them in said spaced apart relationship;
   said arm portions having facing longitudinally extending recesses to form a passageway so that a container lid may move through said passageway;
   an arcuate cut out portion in each of said arm portions to form said at least one opening; and
   said stop means stopping the movement of said container lid through said passageway so that said substantial portion of said upper surface and all of said pull tab are exposed through said at least one opening.

3. Apparatus as in claim 2 and further comprising:
   rotating means for rotating said holding means about a fixed axis;
   mounting means for mounting said holding means on said rotating means for rotation therewith; and control means for controlling the rotation of said rotating means and for stopping said rotation thereof at a plurality of predetermined stations.

4. Apparatus as in claim 3 wherein said plurality of stations comprises:
a first station whereat said passageway in said holding means is located to receive said one container lid from said feeding means and to hold said one container lid to be acted on by said orienting means;
a second station whereat said one container lid is contacted by said force measuring means;
a third station at the end of said force measuring operation; and
a fourth station whereat the opened container lid is discharged.

5. Apparatus as in claim 3 wherein:
said force applying means comprises a pull tab retaining means for retaining said pull tab in a relatively fixed position and said rotating means for rotating said holding means;
said pull tab retaining means having a hook member adapted to be positioned between said pull tab and said upper surface of said container lid;
moving means for moving said hook member between a position removed from said pull tab and a position whereat said hook member is between said pull tab and said upper surface of said container lid;
said force measuring means holding said hook member at a fixed location while measuring the forces being applied thereto; and
said control means rotating said holding means to move at least a portion of said container lid in a direction away from said hook member so that continued rotation of said holding means applies forces on said pull tab to form said opening in said container lid.

6. Apparatus as in claim 5 wherein said stop means comprises:
a pair of spaced apart plates each having an arcuate surface to be contacted by said peripheral rim of said container lid; and
each of said arcuate surfaces having a radius of curvature so that said peripheral rim remains at the same location in said passageway as said container lid is rotated to apply said forces to said pull tab to form said opening in said container lid.

7. Apparatus as in claim 6 and further comprising:
each of said arcuate surfaces having a terminal end portion; and
after said opening in said container lid has been formed, said rotating means rotating said container lid in a direction to move said peripheral rim over said terminal end portions so that said container lid with said opening formed therein moves through said passageway to be discharged from said holding means 8. Apparatus as in claim 6 wherein:
said pull tab is hingedly connected to said container lid for rotation about a fixed axis; and
said axis of rotation of said rotating means coinciding with said axis of rotation of said pull tab.

9. Apparatus as in claim 1 and further comprising:
said orienting means having a body portion;
mounting means for mounting said body portion for reciprocal movement in linear directions;
a pull tab positioning head on said body portion for movement with said body portion so that said pull tab positioning head moves through said opening and into and out of contact with said pull tab and said upper surface of said container lid; and
rotating means for rotating said pull tab positioning head about a longitudinal axis.

10. Apparatus as in claim 9 and further comprising:
said pull tab positioning head having a generally planar surface facing said container lid in said holding means;
a recess having a shape corresponding to said pull tab in said generally planar surface;
control means for positioning said pull tab positioning head so that said recess will always be located at said predetermined location;
resilient means for mounting said pull tab positioning head on said body portion so that said pull tab positioning head will exert a slight resilient force on said pull tab on said container lid in said holding means to push said lower surface of said container lid against portions of said holding means;
said control means rotating said rotating means to rotate said pull tab positioning head through one complete revolution of three hundred and sixty degrees when said pull tab positioning head is in said resilient engagement with said pull tab; and
movement restraining means for restraining movement of said container lid and said pull tab so that said pull tab positioning head rotates relative to said container lid until said pull tab has entered into said recess and thereafter said container lid and said pull tab rotate with said pull tab positioning head so that said pull tab is positioned at said predetermined location.

11. Apparatus as in claim 10 and further comprising:
said holding means comprising a pair of spaced apart arm portions;
securing means for holding said pair of spaced apart arm portions in a spaced apart relationship;
said arm portions having facing longitudinally extending slots to form a passageway so that a container lid may move through said passageway;
said stop means stopping the movement of said container lid through said passageway so that said substantial portion of said upper surface and all of said pull tab are exposed through said opening;
said pull tab positioning head applying said resilient force on said container lid to urge said container lid against portions of said slots; and
said arm portions being formed from a material having a coefficient of friction to provide said restraining means for permitting relative rotation between said pull tab positioning head and said container and said pull tab until said pull tab has entered into said recess but permitting relative rotation between said container lid and said arm portions after said pull tab has entered into said recess.

12. Apparatus as in claim 1 and further comprising:
another opening formed in said holding means so that a substantial portion of said lower surface is exposed; and
printing means located adjacent to said lower surface for printing an identification on said lower surface.

13. Apparatus as in claim 12 and further comprising:
said printing means being mounted on a base support; and support; and
moving means for moving said base support to move said printing means into a position adjacent to said lower surface so as to print on said lower surface and to a position spaced from said holding means so that other operations may be performed on said container lid.

14. Apparatus as in claim 1 wherein said force measuring means comprises:
a load cell assembly mounted on a base member so that it is free to move;
moving means on which said base member is mounted for moving said base member between an operative and an inoperative position;
an angularly shaped lever;
pivot means for pivotally mounting said lever on said load cell assembly;
a hook member on one end of said lever;
moving means connected to the other end of said lever for rotating said lever about said pivot means to move said hook member into and out of a position between said upper surface of said container lid and said pull tab; and
said moving means holding said hook member in a fixed position after said hook member has been moved to said position between said upper surface of said container lid and said pull tab.

15. Apparatus as in claim 14 and further comprising:
rotating means for rotating said holding means about a fixed axis;
mounting means for mounting said holding means on said rotating means for rotation therewith;
control means for controlling the rotation of said rotating means;
said control means rotating said holding means to move said container lid in a direction away from said hook member so that as said container lid continues to be rotated, said hook member applies restraining forces on said pull tab to prevent the movement thereof; and
said load cell assembly measuring said restraining forces during the rotation of said container lid.

16. Apparatus as in claim 15 and further comprising:
means for recording said restraining forces and the angular relationship of said container lid during said rotation of said container lid.

17. Apparatus as in claim 16 and further comprising:
said orienting means having a body portion;
mounting means for mounting said body portion for reciprocal movement in linear directions;
a pull tab positioning head on said body portion for movement with said body portion so that said pull tab positioning head moves through said opening and into and out of contact with said pull tab and said upper surface of said container lid;
rotating means for rotating said pull tab positioning head about a longitudinal axis;
said pull tab positioning head having a generally planar surface facing said container lid in said holding means;
a recess having a shape corresponding to said pull tab in said generally planar surface;
control means for positioning said pull tab positioning head so that said recess will always be located at said predetermined location;
resilient means for mounting said pull tab positioning head on said body portion so that said pull tab positioning head will exert a slight resilient force on said pull tab on said container lid in said holding means to push said lower surface of said container lid against portions of said holding means;
said control means rotating said rotating means to rotate said pull tab positioning head through one complete revolution of three hundred and sixty degrees when said pull tab positioning head is in said resilient engagement with said pull tab; and
movement restraining means for restraining movement of said container lid so that said pull tab positioning head rotates relative to said container lid and said pull tab until said pull tab has entered into said recess and thereafter said container lid and said pull tab rotate with said pull tab positioning head so that said pull tab is positioned at said predetermined location.

18. Apparatus as in claim 17 and further comprising:
said holding means comprising a pair of spaced apart arm portions;
securing means for holding said pair of spaced apart arm portions in a spaced apart relationship;
said arm portions having facing longitudinally extending slots to form a passageway so that a container lid may move through said passageway;
said stop means stopping the movement of said container lid through said passageway so that said substantial portion of said upper surface and all of said pull tab are exposed through said opening;
said pull tab positioning head applying said resilient force on said container lid to urge said container lid against portions of said slots; and
said arm portions being formed from a material having a coefficient of friction to provide said restraining means for permitting relative rotation between said pull tab positioning head and said container and said pull tab until said pull tab has entered into said recess but permitting relative rotation between said container lid and said arm portions after said pull tab has entered into said recess.

19. Apparatus as in claim 18 and further comprising:
another opening formed in said holding means so that a substantial portion of said lower surface is exposed when said container lid is in said holding means;
printing means located adjacent to said lower surface for printing an identification on said lower surface;
said rotating means rotating said pull tab positioning means and said container lid through a second complete revolution of three hundred and sixty degrees; and
said printing means applying said identification to said lower surface during said rotation through said second three hundred and sixty degrees.

20. Apparatus as in claim 18 and further comprising:
said control means stopping the rotation of said rotating means at a plurality of locations comprising:
a first station whereat said passageway in said holding means is located to receive said one container lid from said feeding means and to hold said one container lid to be acted on by said orienting means;
a second station whereat said one container lid is contacted by said force measuring means;
a third station at the end of said force measuring operation; and
a fourth station whereat the opened container lid is discharged.

* * * * *